United States Patent [19]

Tsugita et al.

[11] Patent Number: 5,962,642
[45] Date of Patent: Oct. 5, 1999

[54] METHOD FOR SEQUENCING OF PROTEIN OR PEPTIDE

[75] Inventors: Akira Tsugita, Kashiwa; Keiji Takamoto, Nagareyama; Tatsuaki Ataka, Chiba; Toshihiko Sakuhara, Chiba; Toyoaki Uchida, Chiba, all of Japan

[73] Assignee: Seiko Instruments Inc., Japan

[21] Appl. No.: 08/854,187

[22] Filed: May 9, 1997

[30] Foreign Application Priority Data

May 9, 1996 [JP] Japan ..................................... 8-115087
Jun. 14, 1996 [JP] Japan ..................................... 8-154580

[51] Int. Cl.$^6$ .............................. C07K 1/00; C07K 99/00
[52] U.S. Cl. .......................... 530/345; 530/330; 530/344; 530/402; 530/412
[58] Field of Search .................... 530/330, 344, 530/345, 402, 412

[56] References Cited

U.S. PATENT DOCUMENTS 5,468,843  11/1995  Boyd et al. .............................. 530/345
5,534,440   7/1996  Aebersold et al. ....................... 436/89

FOREIGN PATENT DOCUMENTS 06065220  3/1994  Japan .

*Primary Examiner*—Cecilia J. Tsang
*Assistant Examiner*—C. Delacroix-Muirheid
*Attorney, Agent, or Firm*—Adams & Wilks

[57] ABSTRACT

A protein or peptide which has an amino-terminus serine or threonine which has an acetylated alpha-amino group is allowed to react with an acid, and then allowed to react with an isothiocyanate under acidic conditions to thereby obtain a thiocarbamyl compound. Then the compound is to be analyzed using Edman degradation. Analysis can be performed with fewer operation steps and without using enzymes.

26 Claims, 11 Drawing Sheets

F I G. 2

$$CH_3CO-NHCHCO-\cdots-NHCHCOOH$$
$$\phantom{CH_3CO-NH}|\phantom{CHCO-\cdots-NH}|$$
$$\phantom{CH_3CO-NHC}R_1 \phantom{HCO-\cdots-NHC}R_n$$

$R_1: -CH_2OH$ or $-CH(OH)CH_3$

↓ HFBA or PFPA $$H_2NCHCO-\cdots-NHCHCOOH$$
$$\phantom{H_2NC}|\phantom{HCO-\cdots-NHC}|$$
$$\phantom{H_2NCH}R_1' \phantom{CO-\cdots-NHC}R_n$$

$R_1': -CH_2OCOCH_3$ or $-CH(OCOCH_3)CH_3$

↓ SPITC (acidic media)

$$HO_3S-C_6H_4-NHCS-NHCHCO-\cdots-NHCHCOOH$$
$$\phantom{HO_3S-C_6H_4-NHCS-NHC}|\phantom{HCO-\cdots-NHC}|$$
$$\phantom{HO_3S-C_6H_4-NHCS-NHCH}R_1'\phantom{CO-\cdots-NHC}R_n$$

↓

( Amino acid sequence analysis by Edman degradation )

F I G. 3
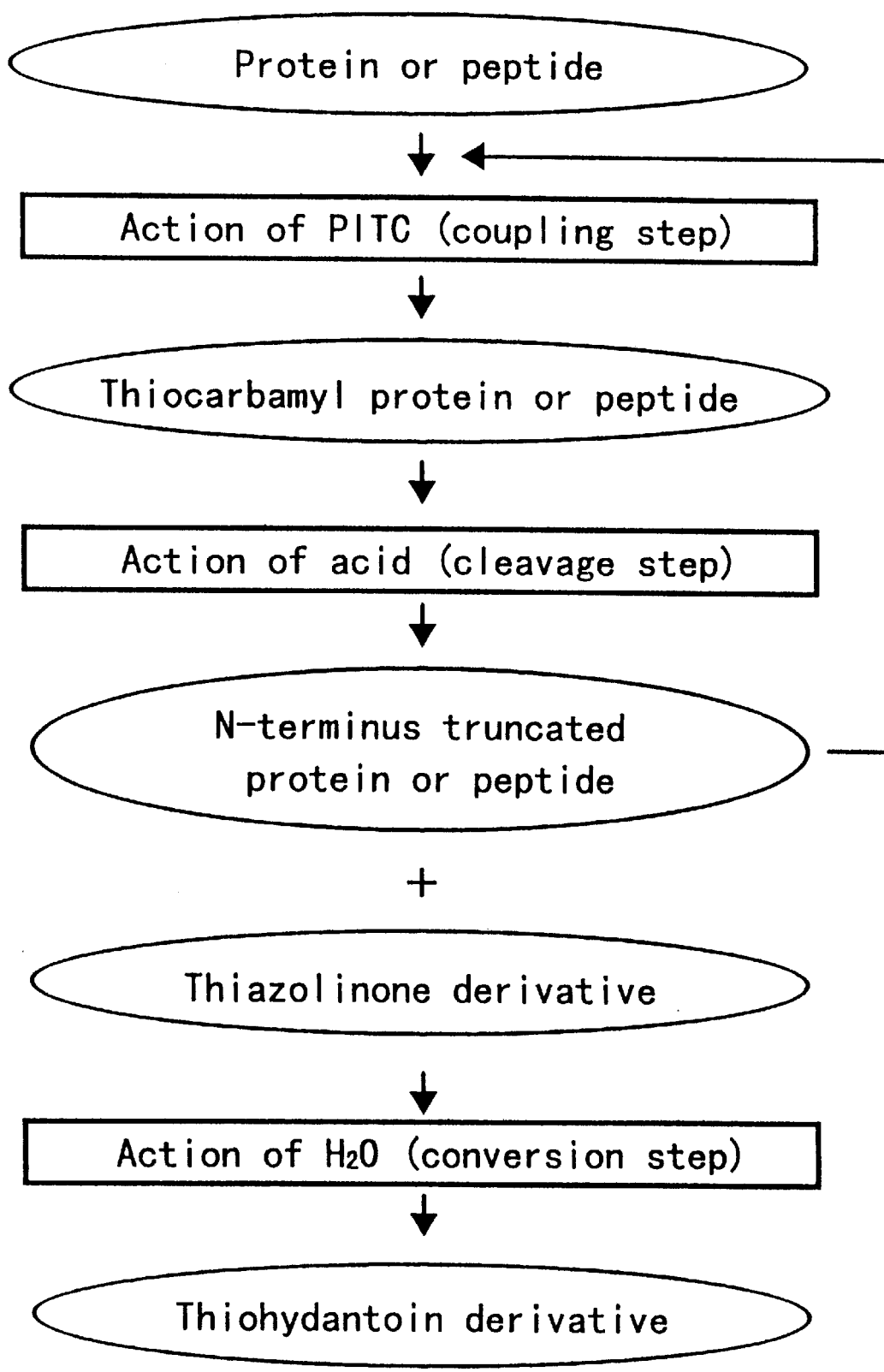

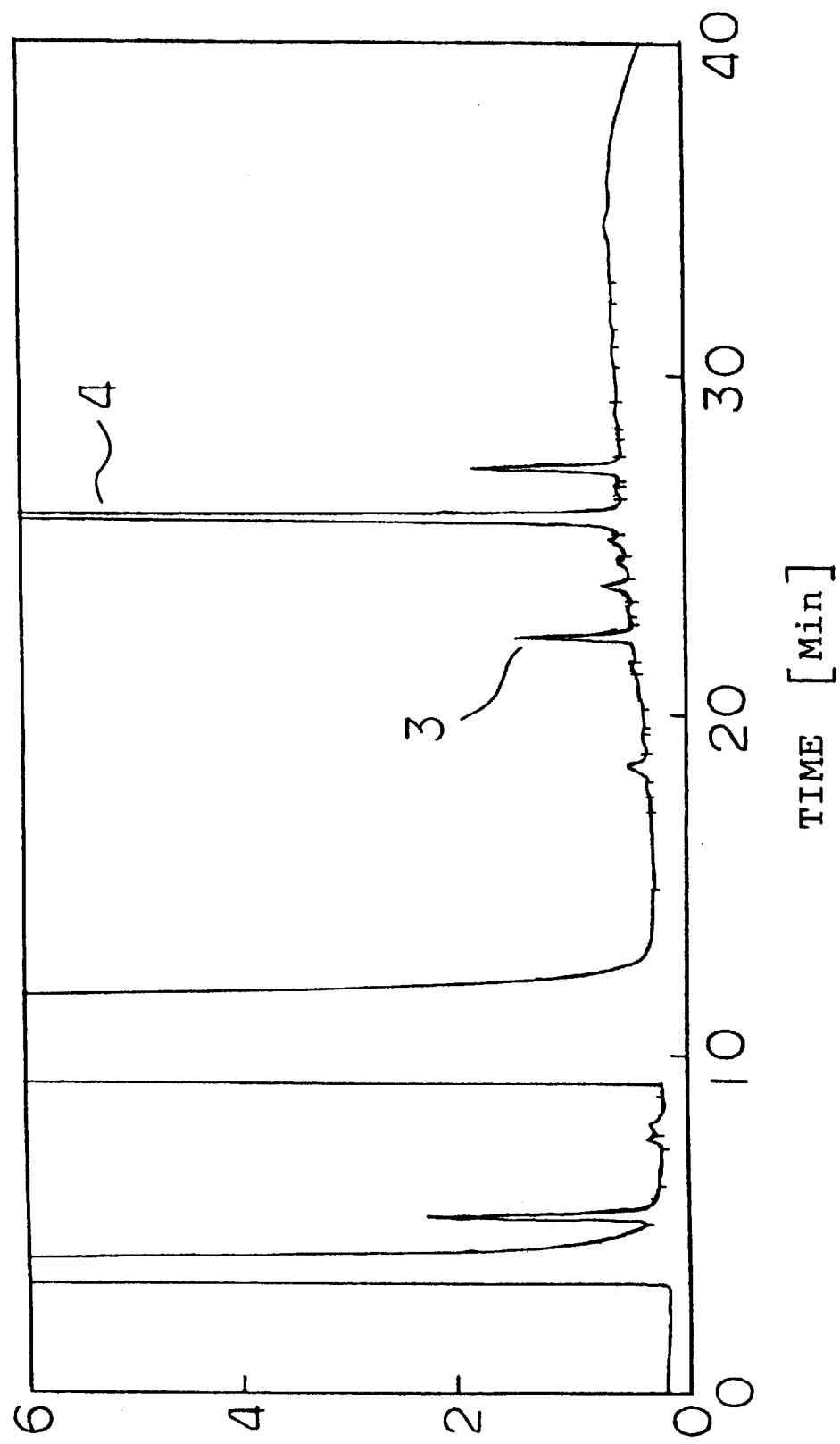

METHOD FOR SEQUENCING OF PROTEIN OR PEPTIDE

BACKGROUND OF THE INVENTION

The present invention relates to a method for analyzing the primary structure of a protein or peptide. Specifically, the present invention relates to a method for sequencing from N-terminal of the protein or peptide, whose α-amino group in the amino terminal (N-terminal) amino acid residue is modified.

It has been clarified that the N-termini of many proteins are modified. It is reported that more than half of the proteins receive some kinds of modifications on the N-termini. Generally, Edman degradation is used for sequencing of protein from the N-terminal amino acid. However, the proteins having modified N-termini cannot be sequenced by Edman degradation.

For example, there are modified proteins (N-acetyl proteins) which have an acetylated α-amino group in the N-terminal amino acid residue. Among proteins which are modified at the N-termini, 80% or more are said to be acetylated. Furthermore, among the N-terminal acetylated proteins, approximately 30% are those to be acetylated at the α-amino group in the N-terminal serine (N-acetylseryl protein), and approximately 10% are those to be acetylated at the α-amino group in the N-terminal threonine (N-acetylthreonyl protein).

Conventionally, to analyze the sequence of amino acids from the N-terminal amino acid of these N-acetyl proteins, the following methods have been reported.

[Conventional Method 1]
(1) Digest an N-acetyl protein with a protease to thereby prepare a mixture of plural peptide fragments.
(2) Allow α-amino groups in newly generated peptide fragments to react with phenylisothiocyanate to thereby form thiocarbamyl compounds.
Here, the N-terminal amino acid of an N-terminal peptide of an original sample protein had been already acetylated and thus do not form a thiocarbamyl compound.
(3) Oxidize the thiocarbamyl compounds with a performic acid to form carbamyl compounds so that they are inert during the process of Edman degradation.
(4) Use an acetylamino acid releasing enzyme to free the acetylated N-terminal amino acid in the N-terminal peptide of the original sample protein.
(5) Thereafter, analyze the sequence of the amino acids by Edman degradation.
In this method, only the N-terminal peptide of the original protein sample is subjected to Edman degradation. (Tsunazawa et al., J. Protein Chem. (1992) vol.11, p382)

[Conventional Method 2]
(1) Digest an N-acetyl protein with a protease to thereby prepare a mixture of plural peptide fragments.
(2) Purify peptide fragments using gel filtration.
(3) From the mixture of peptide fragments, fractionate the N-terminal peptide of the original protein sample using HPLC.
(4) Use an acetylamino acid releasing enzyme to free the acetylated N-terminal amino acid from the N terminal peptide of the original sample protein.
(5) Then sequentially analyze the sequence of amino acids by Edman degradation. (Zoku Seikagaku Jikkenn Kouza 2, Tanpakushitu No Kagaku (Vol.1), Edited by Nihon Seikagakukai, Tokyo Kagaku Dojin, p227)

[Conventional Method 3]
Perform operations 1 to 3 in the Convention Method 2. Analize thus obtained N-terminal peptide of the original sample protein by way of mass spectrometry to analyze the sequence of the amino acid (Zoku Seikagaku Jikkenn Kouza 2, Tanpakushitu No Kagaku (Vol. 1), Edited by Nihon Seikagakukai, Tokyo Kagaku Dojin, p228).

The conventional methods have the following disadvantages: (1) since they require strong reaction conditions, derivatization of samples occur, (2) since they require troublesome operation steps including the use of special devices, thereby being low in yield, and (3) since they use enzymes which have several substrate specificity and activity, an accurate analysis becomes difficult to obtain.

SUMMARY OF THE INVENTION

An object of the present invention is to provide a method for sequencing from the N-terminal of the N-acetylseryl proteins or peptides and the N-acetylthreonyl proteins or peptides (N-acetylseryl or threonyl proteins or peptides) without requiring strong reaction conditions which cause undesired derivatization of samples.

Another object of the invention is to provide a method for sequencing from the N-terminal of the N-acetylseryl proteins or peptides and the N-acetylthreonyl proteins or peptides (N-acetylseryl or threonyl proteins or peptides) without troublesome operations including the use of special devices.

A further object of the invention is to provide a method for sequencing from the N-terminal of the N-acetylseryl proteins or peptides and the N-acetylthreonyl proteins or peptides (N-acetylseryl or threonyl proteins or peptides) without using enzymes.

In order to overcome the above-mentioned problems and to analyze sequence of amino acids, N-acetylseryl or threonyl protein or peptide, according to the present invention, a protein or peptide (O-acethylseryl or threonyl protein or peptide), which has the N-terminal serine or theronine having an acetylated hydroxy group, is allowed to react with an isothiocyanate compound under acidic conditions to thereby obtain a thiocarbamyl compound, and then the thus obtained thiocarbamyl compound is analyzed using Edman degradation. The O-acetylseryl or threonyl protein or peptide is obtained by treating the N-acetylseryl or threonyl protein or peptide with acid.

The above-described means enables the analysis of the amino acid sequence from N-termini of an N-acetylseryl or threonyl protein or peptide, without being required of strong reaction conditions, troublesome steps including the use of special devices, and using enzymes.

BRIEF DESCRIPTION OF THE DRAWINGS

FIG. 2 is a reaction formula which represents an experimental procedure of the present invention;

FIG. 3 is a flow chart of Edman degradation;

FIG. 11 is a result of HPLC analysis performed to investigate the yield of reaction between SPITC and the pentapeptide of Sequence No. 2.

DETAILED DESCRIPTION OF THE INVENTION

The detailed description is made of the present invention with reference to the following examples.

EXAMPLE 1

Figure 1:
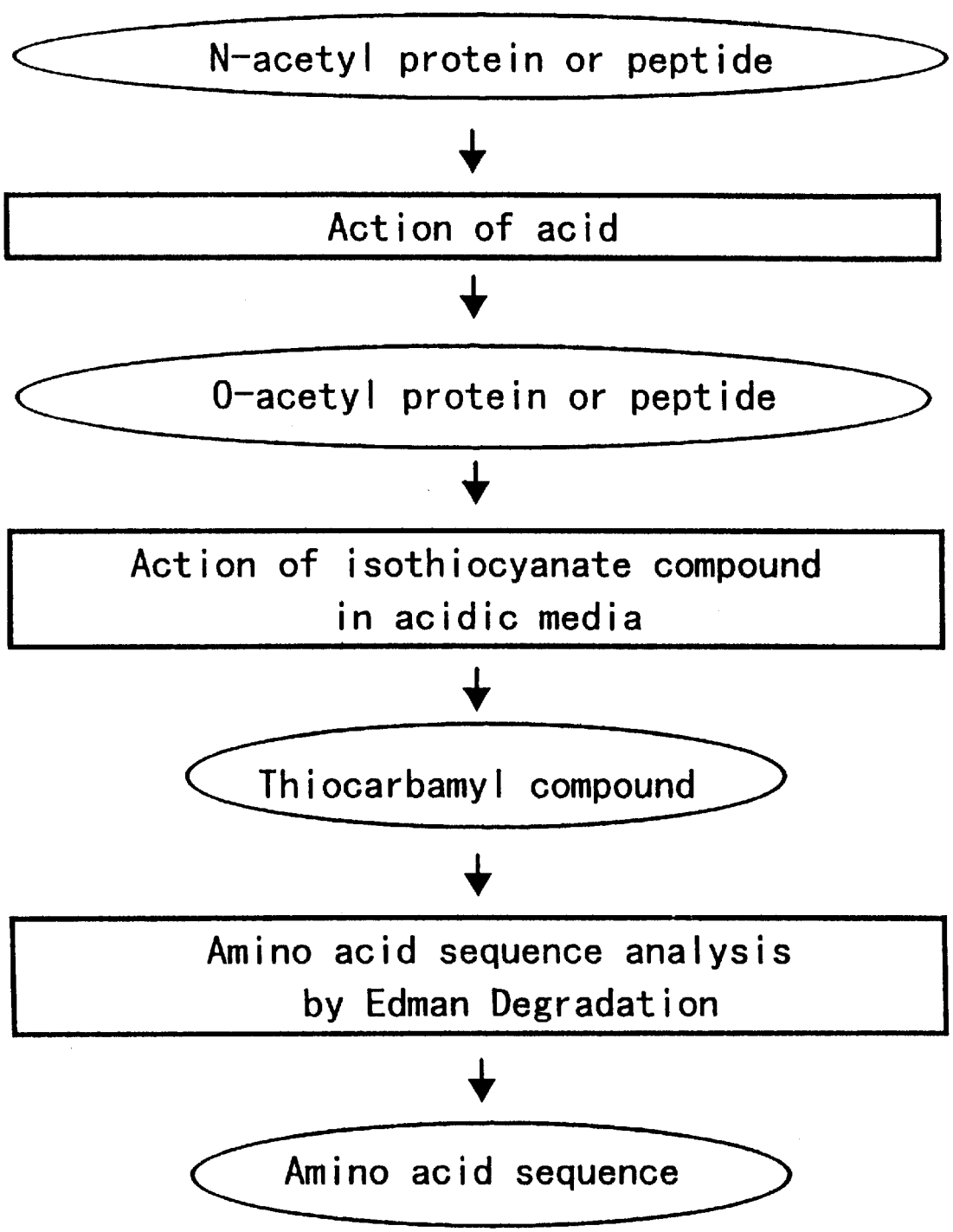
FIG. 1 is a flow chart which represents an analysis method of the present invention.

FIG. 1 shows a flow chart of the analysis method of the present invention. In the drawings, R- represents side chains of amino acids. This symbol denotes the same in the following figures.

First, an N-acetylseryl or threonyl protein or peptide is allowed to react with an acid to obtain an O-acetylseryl or threonyl protein or peptide. Then, the thus obtained O-acetylseryl or threonyl protein or peptide is allowed to react with an isothiocyanate compound represented by $\phi$-NCS under acidic conditions to thereby obtain a thiocarbamyl compound.

Thereafter the thus obtained sample is analyzed by Edman degradation to determine the sequence of amino acids from N-termini, the N-acetylseryl or threonyl protein or peptide.

EXAMPLE 2

Here, the detailed description is made of one example of the experimental method.

Operation procedure for sequencing of the present invention is as follows. (refer to FIG. 2) Place a portion or sample solution containing an N-acetylseryl or threonyl protein or peptide, or a membrane retaining N-acetylseryl or threonyl protein or peptide, into a tube and allow them to dry. Add an acid solution to the tube, seal the tube with cap, and then allow the acid to act.

Reaction conditions
Acid solution: 75% pentafluoropropionic acid (PFPA) aqueous solution
Reaction temperature: 50° C.
Reaction period: one hour In this reaction, instead of PFPA, other acids including heptafluorobutyric acid (HFBA) can be used. During this reaction process, the acid acts on the N-acetylseryl or threonyl protein or peptide, thereby forming the O-acetylseryl or threonyl protein or peptide.

Then allow the sample in the tube to dry.
Next, add a solution containing an isothiocyanate compound to react with the sample.

Reaction conditions
Isothiocyanate compound: 4-sulfophenylisothiocyanate (SPITC) $HO_3S$—$C_6H_4$—NCS
SPITC concentration: 0.5%
Solvent: mixture of 0.1M pyridine-acetate buffer (pH 6.0) and acetonitrile (3:2)
Reaction temperature: 50° C.
Reaction period: 30 minutes In this reaction, instead of SPITC, other isothiocyanates including a trimethylisothiocyanate can be used. During this reaction process, an isothiocyanate acts on the O-acethylseryl or threonyl protein or peptide to thereby form the thiocarbamyl compound.

The thus obtained sample is to be analyzed using Edman degradation, and the amino acid sequence of the protein or peptide can be analyzed by identifying the thus obtained series of thiohydantoin compounds.

Since the procedure of Edman degradation is widely known, and therefore, description thereof is omitted.

EXAMPLE 3

In this example, it will be shown that the amino acid sequence analysis of thiocarbamyl compounds obtained through operations described in Example 2 can be performed using Edman degradation (Refer to FIG. 3). As a sample of an analysis, a heptapeptide of Sequence No. 1 acetylseryl-glutamoyl-asparaginyl-proryl-thyrosylvalyl-valinamide (Ac-Ser-Gln-Asn-Pro-Tyr-Val-Val-NH$_2$) is used.

Figure 4:
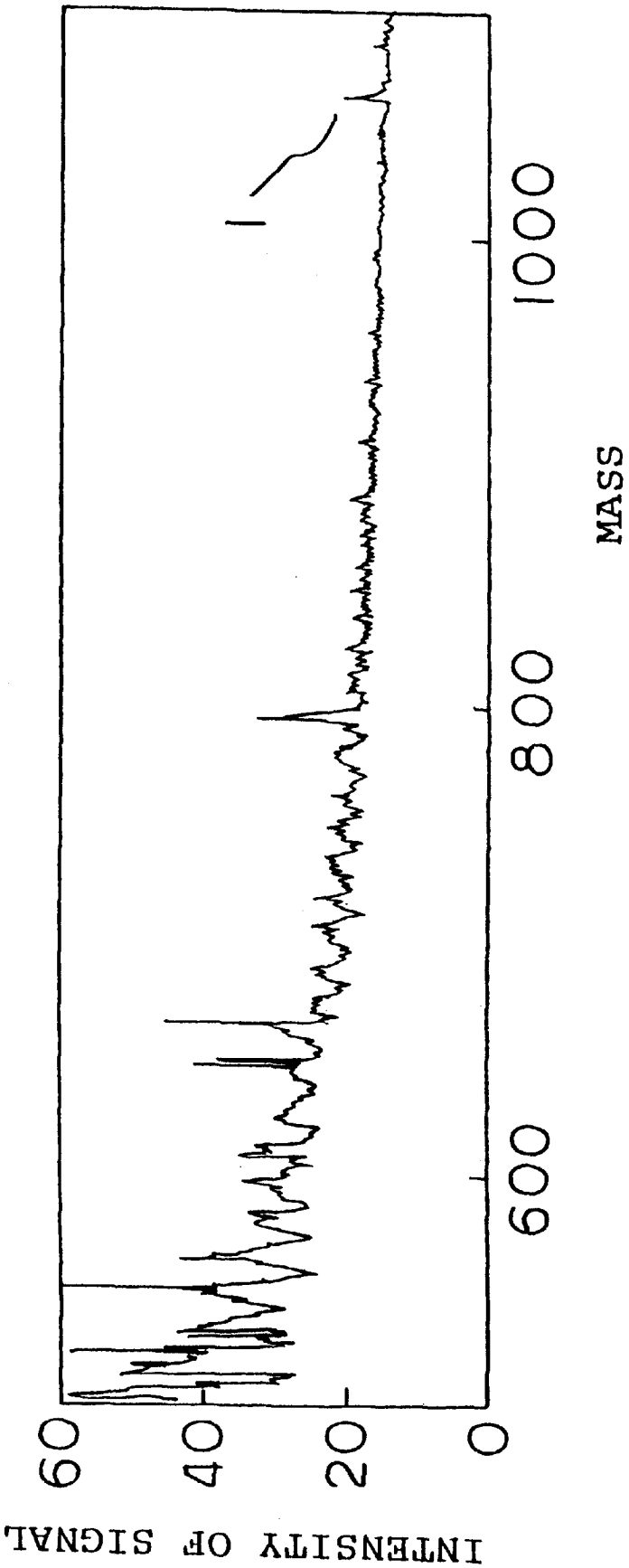
FIG. 4 as a result of mass spectrometry of a thiocarbamyl compound.

FIG. 4 shows a result of mass spectrometry of obtained thiocarbamyl compounds. A sign 1 shows a signal from the molecular ion corresponding to a thiocarbamyl compound (molecular weight of 1062) obtained when allowing SPITC to react with an O-acetyl peptide corresponding to a heptapeptide of Sequence No. 1.

Conditions for mass spectrometry are as follows. Conditions for mass spectrometry Analytical instrument: Mass spectrometer HX-110 (Nihon Denshi)
Measurement conditions:
Accelerating voltage 10 kV
Resolution 1,000
Ion source FAB (fast atom bombardment method)
Ionizaion gas Xe
Ion mode cation
FAB gun accelerating voltage 6 kV
Detection unit MULTIPLIER
Load voltage −20 kV
Data processing system DA5000
Matrix glycerol:thioglycerol:m-nitrobenzyl alchol=1:1:1
Procedure for sample preparation (1) Dry a sample with vacuum.
(2) Dissolve the sample in 67% of acetic acid (or dimethylformamide) aqueous solution.
(3) Add an aliquot of 1 µl of matrix on the target.
(4) Add an aliquot of 1 µl of the sample solution on the target, and allow them to mix.
(5) Introduce the sample to the ion source.

A molecular ion corresponding to a thiocarbamyl compound (molecular weight of 1062) obtained when allowing SPITC to react with the O-acetyl peptide corresponding to the heptapeptide of Sequence No. 1 was detected.

Next, treat this compound with trifluoroacetic acid. As shown in FIG. 3, this is the cleavage step in Edman degradation used for the analysis of amino acid sequence. That is, this is the step in which acid specifically cleaves the peptide bond between a first and a second amino acid residues at the N-terminal end of a thiocarbamyl protein or a peptide that was formed by reacting an isothiocyanate compound on α-amino group in the N-terminal amino acid of a protein or peptide.

The reaction conditions are as follows.

Figure 5:
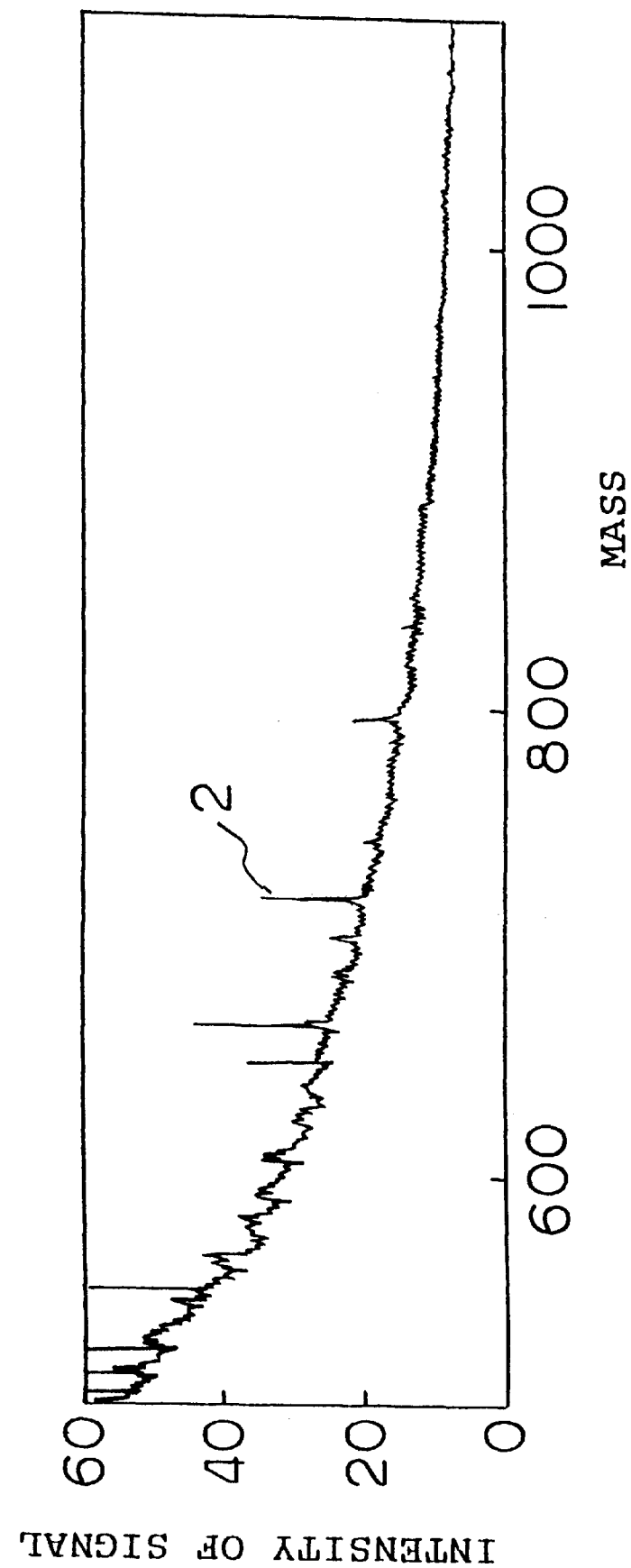
FIG. 5 is a result of mass spectrometry of the compound obtained by an acid-treatment of thiocarbamyl compound.

Reaction conditions
Reaction reagent: trifluoroacetic acid (anhydrous)
Reaction time: 50° C.
Reaction period: 30 minutes FIG. 5 shows a result of the mass spectrometry of thus obtained compounds. A sign 2 shows a signal from the molecular ion corresponding to a hexapeptide (molecular weight of 717) which is formed by being removed an N-terminal acetylated serine from the heptapeptide of Sequence No. 1.

Conditions for mass spectrometry are the same as above-mentioned conditions.

The molecular ion corresponding to a thiocarbamyl compound (molecular weight of 1062) obtained when allowing SPITC to react with the O-acetyl peptide corresponding to the heptapeptide of Sequence No. 1 was no more detected and detected, instead was a molecular ion corresponding to a hexapeptide (molecular weight of 717) which is formed by removing the N-terminal acetylated serine from the original sample heptapeptide, glutamyl-asparaginyl-prolyl-thyrosylvalyl-valinamide (Gln-Asn-Pro-Tyr-Val-Val-NH$_2$).

Accordingly, it can be understood that amino acid sequence can be determined by analyzing subsequently obtained thiocarbamyl compounds with Edman degradation in this example, based on the fact that the hexapeptide, glutamyl-asparaginyl-prolyl-thyrosyl-valyl-valinamide (Gln-Asn-Pro-Tyr-Val-Val-NH$_2$), which lacks the amino N-terminal acetylated serine from the original sample heptapeptide of Sequence No. 1 is obtained, it is understood that SPITC reacted with the α-amino group in N-terminal amino acid of the O-acetyl peptide corresponding to the heptapeptide of Sequence No.1 to thereby form a corresponding thiocarbamyl compound, and that in the prior step, after the heptapeptide of Sequence No. 1 (N-acetyl peptide) was treated with acid, the O-acetyl peptide corresponding to the heptapeptide of Sequence No. 1 was formed and an α-amino group appeared.

EXAMPLE 4

In this example, a result of investigation on reaction conditions for the reaction between SPITC and α-amino group of N-terminal amino acids to thereby form corresponding thiocarbamyl compounds, is shown.

As a test sample, a pentapeptide of Sequence No. 2, leucyl-tryptophanyl-methionyl-arginyl-phenylalanin (Leu-Trp-Met-Arg-Phe) was used.

The following reaction conditions were used.

Reaction conditions
SPITC concentration: 0.5%
Reaction solvent:
Buffer solution: 0.1M prydine-acetate buffer solution (1) pH 4.0, (2) pH 5.5, (3) pH 6.03

Mixture with organic solvent: (1) not mixed, (2) buffer solution was mixed with acetonitrile at the ratio of 3:2.
Reaction temperature: 50° C.
Reaction period: 30 minutes Experimental procedure was as follows.
(1) Allow to react the pentapeptide of Sequence No. 2 with SPITC under each of the above various conditions.
(2) Analyze the reaction products using high-performance liquid chromatography (HPLC).
(3) Compare the peak area obtained from non-react pentapeptide of Sequence No. 2 (performed to as A) with the sum of the peak area obtained from non-react pentapeptide of Sequence No. 2 and the peak area of the reaction product between SPITC and the pentapeptide of Sequence No. 2 (B).

Calculation formula for reaction yield (%) is as follows.

(1−A/A+B)×100

Conditions of HPLC analysis are as follows.

Column: Shiseido CAPSELPAC C-18
Concentration gradient elution:

A solution 0.1% TFA aqueous solution
B solution aqueous solution containing 80% of methanol and 0.1% TFA
0–5 minutes B solution 20%
5–25 minutes B solution 20%→100% (linear)
25–40 minutes B solution 100[{]ps
Detention: Absortion 280 nm Peaks were identified by mass spectrometry. Conditions for mass spectrometry was the same with those described in Example 3.

Results are shown in FIGS. 6 to 11. A reference numeral 3 shows a peak corresponding to a pentapeptide of Sequence No. 2. A reference numeral 4 shows a peak corresponding to the reaction product between SPITC and the pentapeptide of Sequence No. 2.

Following Table 1 lists combinations of conditions and each Figure showing results.

TABLE 1

Figure 6:
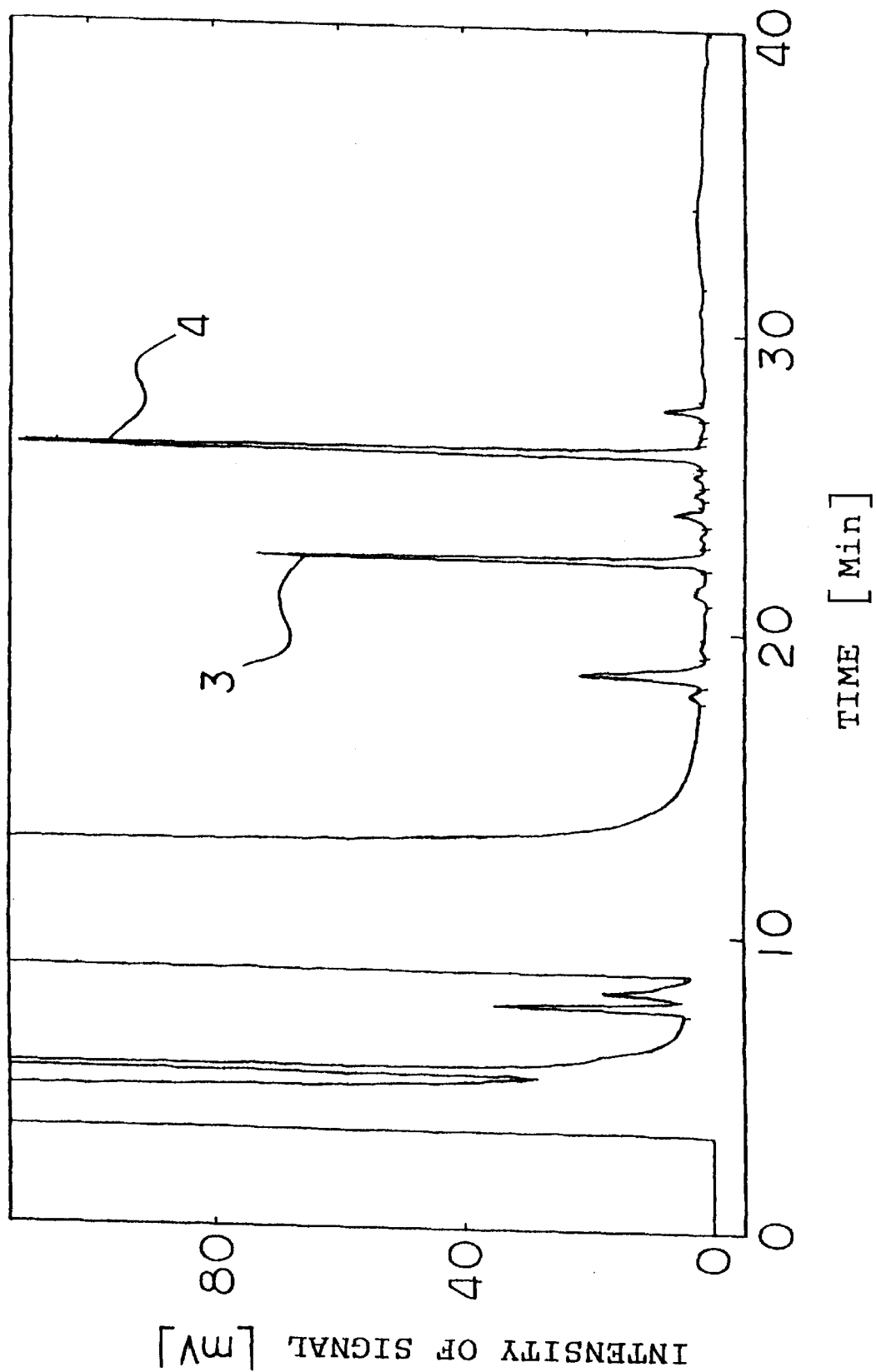
FIG. 6 is a result of HPLC analysis performed to investigate the yield of reaction between SPITC and the pentapeptide of Sequence No. 2.
Figure 7:
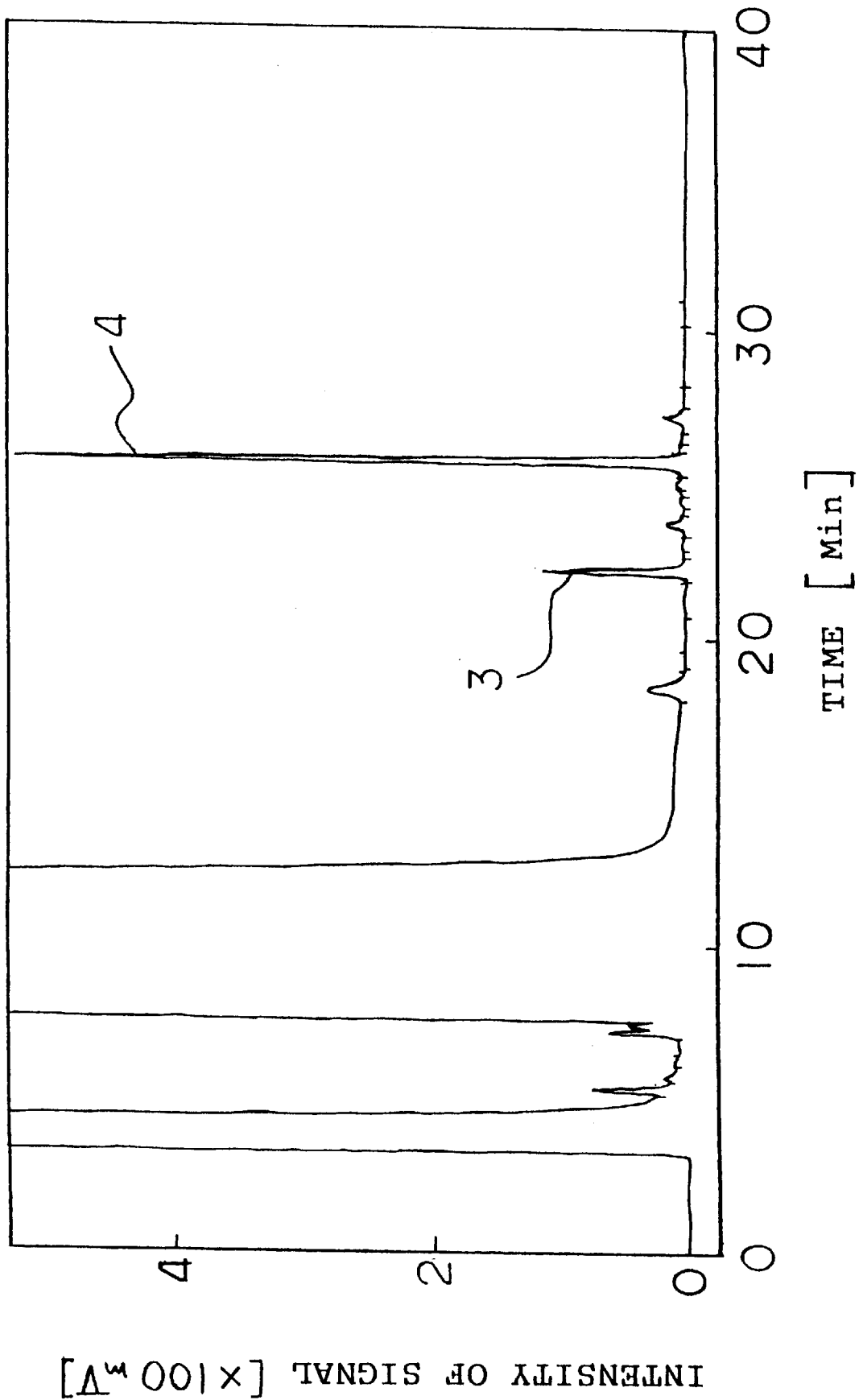
FIG. 7 is a result of HPLC analysis performed to investigate the yield of reaction between SPITC and the pentapeptide of Sequence No. 2.
Figure 8:
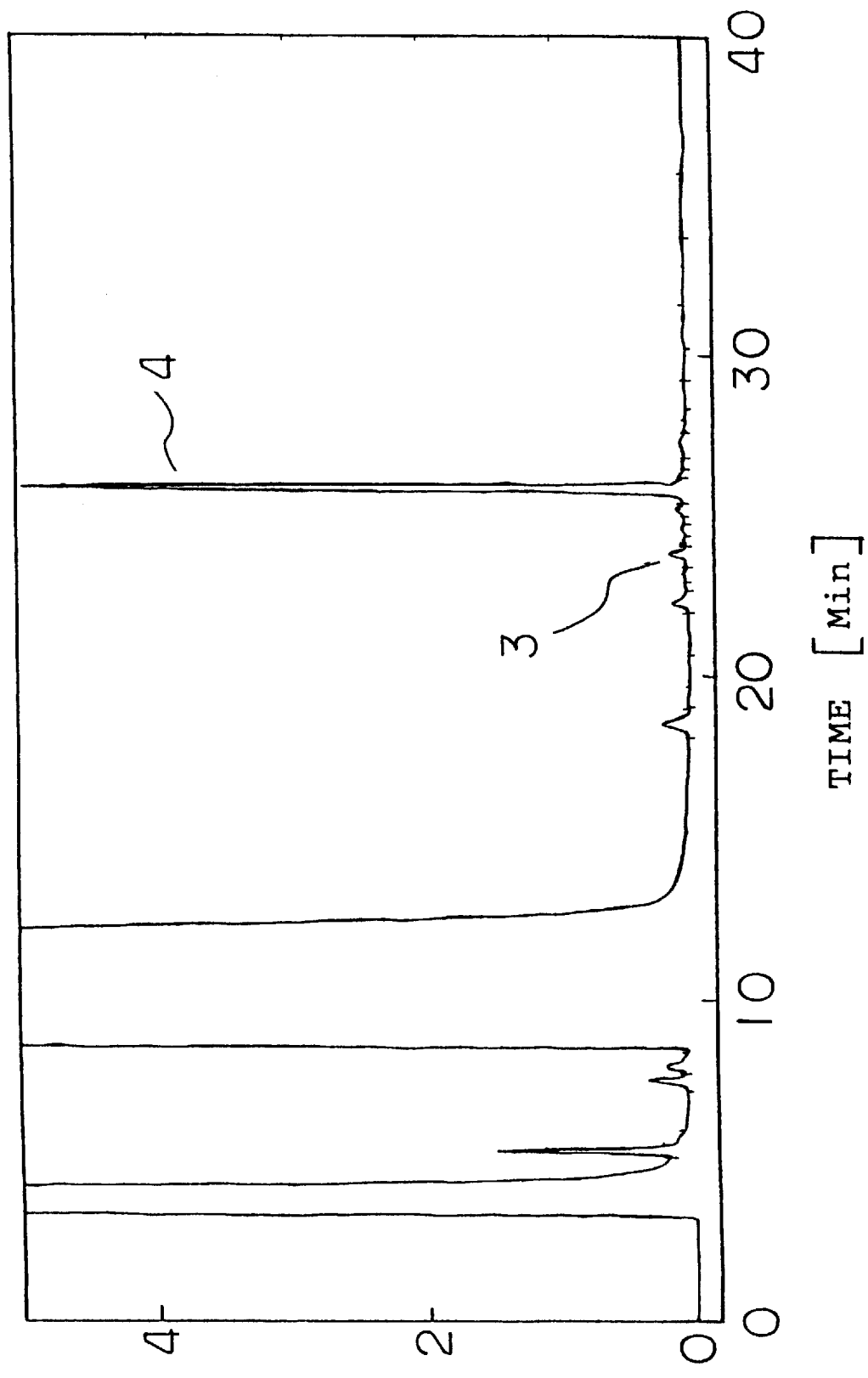
FIG. 8 is a result of HPLC analysis performed to investigate the yield of reaction between SPITC and the pentapeptide of Sequence No. 2.
Figure 9:
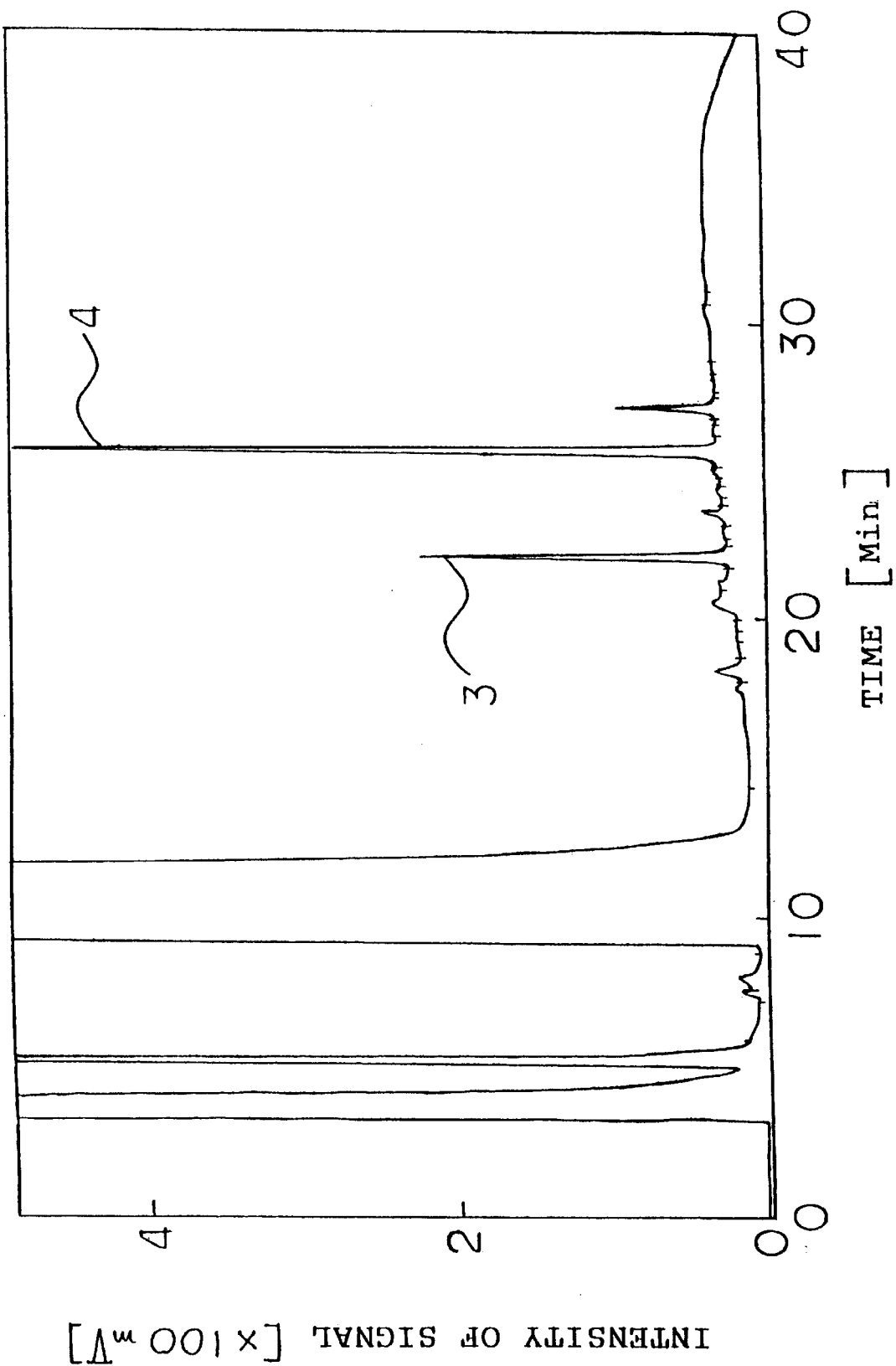
FIG. 9 is a result of HPLC analysis performed to investigate the yield of reaction between SPITC and the pentapeptide of Sequence No. 2.
Figure 10:
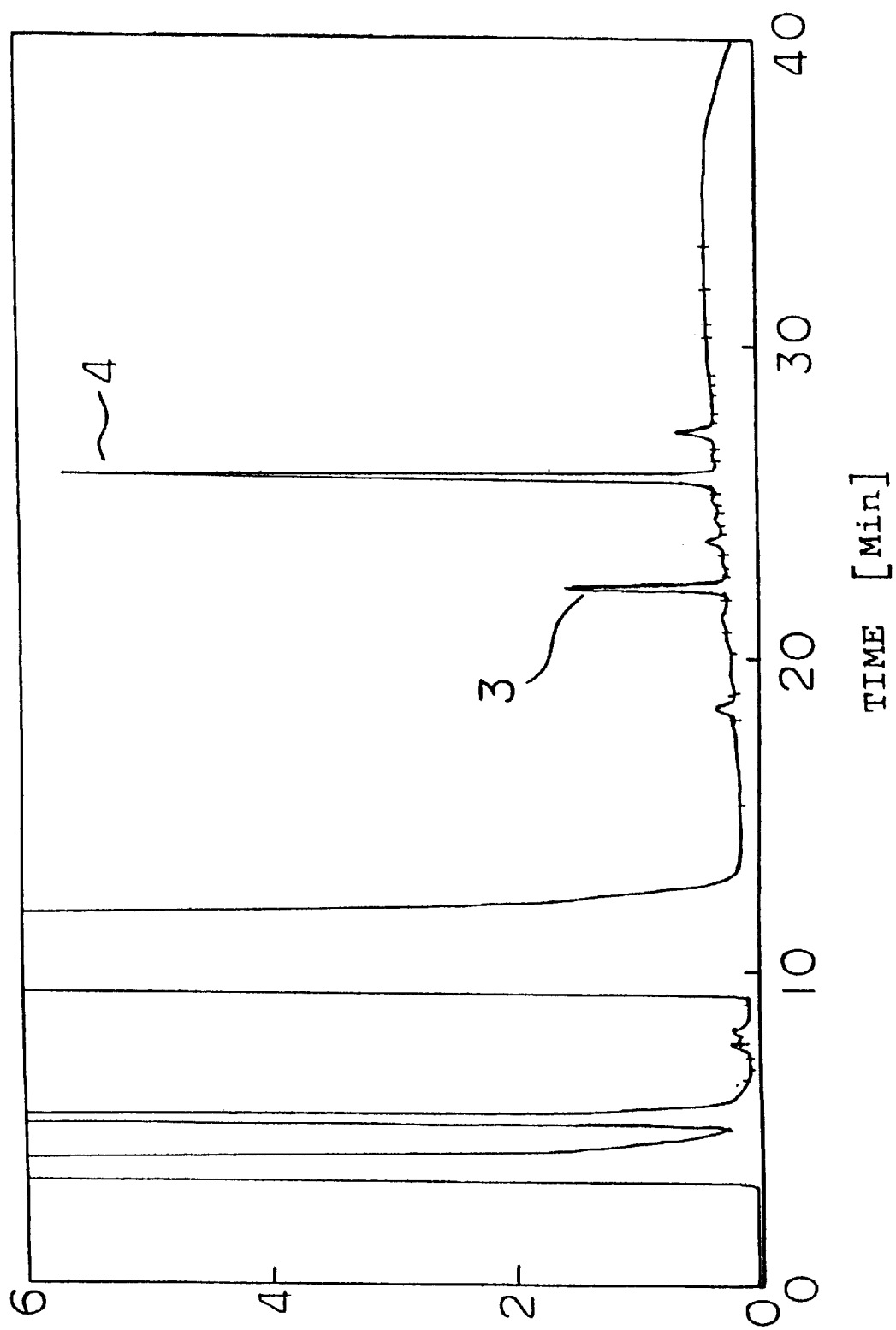
FIG. 10 is a result of HPLC analysis performed to investigate the yield of reaction between SPITC and the pentapeptide of Sequence No. 2.

|  | Solution | Ph |
| --- | --- | --- |
| FIG. 6 | buffer solution | 4.0 |
| FIG. 7 | buffer solution | 5.5 |
| FIG. 8 | buffer solution | 6.0 |
| FIG. 9 | buffer + acetonitrile | 4.0 |
| FIG. 10 | buffer + acetonitrile | 5.5 |
| FIG. 11 | buffer + acetonitrile | 6.0 |

Following Table 2 lists reaction yield.

| PH | 4.0 | 5.5 | 6.0 |
| --- | --- | --- | --- |
| buffer | 61.2% | 82.7% | 97.6% |
| buffer + acetonitrile (3:2) | 60.2% | 75.9% | 89.0% |

As the table shows, for both the reaction solution systems, the system used buffer of pH 6.0 had a higher yield.

Among the above solution systems, the solution consisting of buffer (pH 6.0) mixed with the acetonitrile at the above-mentioned ratio, which is more impregnable into membrane used in the amino acid sequence analysis was used in the above Example.

Above mentioned results are summarized as follows.
According to the present invention, in order to analyze the sequence from the N-termini of a protein or peptide which has an N-terminal serine or threonine having an acetylated α-amino group (an N-acetylseryl or threonyl protein or peptide), an O-acetylseryl or threonyl protein or peptide is allowed to react with an isothiocyanate compound under acidic conditions to thereby obtain a thiocarbamyl compound, and there is thus obtained a thiocarbamyl compound which is analyzed by Edman degradation. The O-acetylseryl or threonyl protein or peptide is prepared by treating the N-acetylseryl or threonyl protein or peptide with acid.

This method enables the determination of amino acid sequence from N-terminus of the N-acetylseryl or threonyl protein or peptide.

The important points of the present invention are as follows.

In order to determine the amino acid sequence of the N-terminus of a protein or peptide which has an N-terminal serine or threonine with an acetylated α-amino group (an N-acetylseryl or threonyl protein or peptide), an O-acetylseryl or threonyl protein or peptide is allowed to react with an isothiocyanate compound under acidic conditions to thereby obtain a thiocarbamyl compound, and there is obtained a thiocarbamyl compound which is analyzed by Edman degradation. The O-acetylseryl or threonyl protein or peptide is prepared by treating the N-acetylseryl or threonyl protein or peptide with acid.

The present invention enables the determination of the amino acid sequence from N-terminus of an N-acetylseryl or threonyl protein or peptide, without troublesome steps including the use of special devices, and without using enzymes or causing undesired derivitization.

Therefore, the method for determining the amino acid sequence from N-terminus of a protein or peptide according to the present invention is very valuable in industrial field.

What is claimed is:

1. A method for the sequencing of a protein or a peptide, comprising the steps of:
    treating one of a first protein and a first peptide, the selected one of which has an amino-terminal amino acid residue having an acetylated α-amino group, with an acid to form one of a second protein or a second peptide each of which has an amino-terminal amino acid residue having an acetylated hydroxyl group,
    treating one of the second protein or the second peptide with an isothiocyanate compound in the presence of an acid surrounding the selected one of the second protein or the second peptide to form a thiocarbamyl protein or peptide; and
    treating the thiocarbamyl protein or peptide by Edman degradation.

2. A method for the sequencing of a protein or a peptide according to claim 1; wherein the selected first protein or first peptide comprises one of an N-acetylseryl protein or peptide and an N-acetylthreonyl protein or peptide.

3. A method for the sequencing of a protein or a peptide according to claim 1; wherein the selected first protein or first peptide comprises a heptapeptide having the sequence acetylseryl-glutamoyl-asparaginyl-prolyl-Ayrosyl-valyl-valinamide (Ac-Ser-Gln-Asn-Pro-Tyr-Val-Val-NH$_2$).

4. A method for the sequencing of a protein or a peptide according to claim 1; wherein the second protein or the second peptide comprises an O-acetylseryl or threonyl peptide which has an N-terminal serine or threonine having the acetylated hydroxyl group.

5. A method for the sequencing of a protein or a peptide according to claim 1; wherein the step of treating one of a first protein and a first peptide with an acid comprises the step of treating the selected first protein or peptide with an acid solution comprising pentafluoropropionic acid.

6. A method for the sequencing of a protein or a peptide according to claim 5; wherein the acid solution is an aqueous solution comprising 75% pentafluoropropionic acid (PFPA) at 50° C. for one hour.

7. A method for the sequencing of a protein or a peptide according to claim 1; wherein the step of treating one of the second protein or the second peptide with an isothiocyanate compound to form a thiocarbamyl protein or peptide comprises the step of treating the second protein or second peptide with an isothiocyanate compound represented by Φ-NCS.

8. A method for the sequencing of a protein or a peptide according to claim 1; wherein the step of treating one of a first protein and a first peptide with an acid comprises the step of treating the selected first protein or peptide with an acid solution containing heptafluorobutyric acid.

9. A method for the sequencing of a protein or a peptide according to claim 1; wherein the isothiocyanate compound comprises 4-sulfophenylisothiocyanate.

10. A method for the sequencing of a protein or a peptide according to claim 1; wherein the isothiocyanate compound comprises trimethylisothiocyanate.

11. A method for the sequencing of a protein or a peptide according to claim 1; wherein the step of treating one of the second protein or the second peptide with an isothiocyanate compound comprises the step of adding to the second protein or the second peptide an isothiocyanate compound solution comprising 4-sulfophenylisothiocyanate and a mixture of 0.1M pyridine-acetate buffer having a pH of 6.0 and acetonitrile.

12. A method for the sequencing of a protein or a peptide according to claim 1; wherein the step of treating the thiocarbamyl protein or peptide by Edman degradation comprises the steps of treating the thiocarbamyl protein or peptide with trifluoroacetic acid to cleave a peptide bond between first and second amino acid residues at the N-terminal end of the thiocarbamyl protein or peptide that was formed by reacting the isothiocyanate compound on the α-amino group in the N-terminal amino acid of the selected first protein or first peptide.

13. A method for the sequencing of a protein or a peptide according to claim 1; wherein the selected first protein or first peptide comprises a hexapeptide having the sequence leucyl-tryptophanyl-methionyl-arginyl-phenylalanine (Leu-Trp-Met-Arg-Phe).

14. A method for the sequencing of a protein or a peptide comprising the steps of:

treating one of a first protein and a first peptide, the selected one of which has an amino-terminal amino acid residue having an acetylated α-amino group, with an acid to form one of a second protein and a second peptide, each of which has an amino-terminal amino acid residue having an acetylated hydroxyl group;

treating one of the second protein and the second peptide with an isothiocyanate compound to form a thiocarbamyl protein or peptide; and treating the thiocarbamyl protein or peptide by Edman degradation.

15. A method for the sequencing of a protein or a peptide according to claim 14; wherein the selected first protein or first peptide comprises one of an N-acetylseryl protein or peptide and an N-acetylthreonyl protein or peptide.

16. A method for the sequencing of a protein or a peptide according to claim 14; wherein the selected first protein or first peptide comprises a heptapeptide having the sequence acetylseryl-glutamoyl-asparaginyl-prolyl-tyrosyl-valyl-valinamide (Ac-Ser-Gln-Asn-Pro-Tyr-Val-Val-NH$_2$).

17. A method for the sequencing of a protein or a peptide according to claim 14; wherein the second protein or the second peptide comprises an O-acetylseryl or threonyl peptide which has an N-terminal serine or threonine having the acetylated hydroxyl group.

18. A method for the sequencing of a protein or a peptide according to claim 14; wherein the step of treating one of a first protein and a first peptide with an acid comprises the step of treating the selected first protein or peptide with an acid solution comprising pentafluoropropionic acid.

19. A method for the sequencing of a protein or a peptide according to claim 18; wherein the acid solution is an aqueous solution comprising 75% pentafluoropropionic acid (PFPA) at 50° C. for one hour.

20. A method for the sequencing of a protein or a peptide according to claim 14; wherein the step of treating one of the second protein or the second peptide with an isothiocyanate compound to form a thiocarbamyl protein or peptide comprises the step of treating the second protein or second peptide with an isothiocyanate compound represented by Φ-NCS.

21. A method for the sequencing of a protein or a peptide according to claim 14; wherein the step of treating one of a first protein and a first peptide with an acid comprises the step of treating the selected first protein or peptide with an acid solution containing heptafluorobutyric acid.

22. A method for the sequencing of a protein or a peptide according to claim 14; wherein the isothiocyanate compound comprises 4-sulfophenylisothiocyanate.

23. A method for the sequencing of a protein or a peptide according to claim 14; wherein the isothiocyanate compound comprises trimethylisothiocyanate.

24. A method for the sequencing of a protein or a peptide according to claim 14; wherein the step of treating one of the second protein or the second peptide with an isothiocyanate compound comprises the step of adding to the second protein or the second peptide an isothiocyanate compound solution comprising 4-sulfophenylisothiocyanate and a mixture of 0.1M pyridine-acetate buffer having a pH of 6.0 and acetonitrile.

25. A method for the sequencing of a protein or a peptide according to claim 14; wherein the step of treating the thiocarbamyl protein or peptide by Edman degradation comprises the steps of treating the thiocarbamyl protein or peptide with trifluoroacetic acid to cleave a peptide bond between first and second amino acid residues at the N-terminal end of the thiocarbamyl protein or peptide that was formed by reacting the isothiocyanate compound on the α-amino group in the N-terminal amino acid of the selected first protein or first peptide.

26. A method for the sequencing of a protein or a peptide according to claim 14; wherein the selected first protein or first peptide comprises a hexapeptide having the sequence leucyl-tryptophanyl-methionyl-arginyl-phenylalanine (Leu-Trp-Met-Arg-Phe).

* * * * *

```
                        SEQUENCE LISTING (1) GENERAL INFORMATION:

(iii) NUMBER OF SEQUENCES:  2

(2) INFORMATION FOR SEQ ID NO: 1:

(i) SEQUENCE CHARACTERISTICS:
           (A) LENGTH:  7
           (B) TYPE:   amino acid
           (C) STRANDEDNESS: Not Applicable
           (D) TOPOLOGY:  linear (ii) MOLECULE TYPE:  peptide (xi) SEQUENCE DESCRIPTION: SEQ ID NO:   1:

Ser Gln Asn Tyr Pro Val Val
  1               5

(2) INFORMATION FOR SEQ ID NO: 2:

(i) SEQUENCE CHARACTERISTICS:
           (A) LENGTH:  5
           (B) TYPE:   amino acid
           (C) STRANDEDNESS: Not Applicable
           (D) TOPOLOGY:  linear (ii) MOLECULE TYPE:  peptide (xi) SEQUENCE DESCRIPTION: SEQ ID NO:   2:

Leu Trp Met Arg Phe
  1               5
```